(12) United States Patent
Lorraine et al.

(10) Patent No.: US 7,150,193 B2
(45) Date of Patent: Dec. 19, 2006

(54) METHOD FOR DETECTION OF DEFECTS IN ANISOTROPIC MATERIALS

(75) Inventors: Peter William Lorraine, Niskayuna, NY (US); Ronald Alan Kline, Norman, OK (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/747,739

(22) Filed: Dec. 29, 2003
(Under 37 CFR 1.47)

(65) Prior Publication Data

US 2005/0139006 A1    Jun. 30, 2005

(51) Int. Cl.
*G01N 29/18* (2006.01)
(52) U.S. Cl. .............................. 73/597; 73/602; 73/655
(58) Field of Classification Search ................. 73/602, 73/655, 656, 657, 625, 626, 597, 598, 600, 73/649; 356/357, 358, 432 T, 354
See application file for complete search history.

(56) References Cited

U.S. PATENT DOCUMENTS

| | | | |
|---|---|---|---|
| 5,458,120 A | 10/1995 | Lorraine | 600/472 |
| 5,476,010 A | 12/1995 | Fleming et al. | 73/620 |
| 5,477,736 A | 12/1995 | Lorraine | 73/642 |
| 5,672,830 A * | 9/1997 | Rogers et al. | 73/597 |
| 5,760,904 A | 6/1998 | Lorraine et al. | 356/513 |
| 5,801,312 A | 9/1998 | Lorraine et al. | 73/602 |
| 5,951,479 A | 9/1999 | Holm et al. | 600/447 |
| 6,128,081 A * | 10/2000 | White et al. | 356/503 |
| 6,142,019 A | 11/2000 | Venchiarutti et al. | 73/602 |
| 6,182,512 B1 | 2/2001 | Lorraine | 73/655 |
| 6,220,099 B1 | 4/2001 | Marti et al. | 73/633 |
| 6,769,307 B1 * | 8/2004 | Dixon et al. | 73/602 |
| 2003/0033878 A1 | 2/2003 | Dubois et al. | |
| 2003/0067249 A1 | 4/2003 | Lockwood et al. | |

FOREIGN PATENT DOCUMENTS

EP    1 057 012 B1    11/2003
WO    WO 99/41600    8/1999

OTHER PUBLICATIONS

"Saft for Anisotropic Media" http://sdcmr.sdsu.edu/saft.htm Nov. 11, 2003, 2 pages.
Yoshikawa et al. "Crystal Structure and Hydrogen Occupation in $HxV2O5(x=0.0-3.9)$" Journal of Materials Science 29 (1994) 1319-1323.
Dubois et al. "Progress on the Development of an Advanced Laser Ultrasound Generation Source for Inspecting Polymer-Matrix Composites" Review of Quantitative Nondestructive Evaluation, vol. 21, edited by D.O. Thompson and D.E. Chimenti, 2002 American Institute of Physics, 300-307.

(Continued)

*Primary Examiner*—Hezron Williams
*Assistant Examiner*—Jacques saint-Surin
(74) *Attorney, Agent, or Firm*—Fletcher Yoder

(57) ABSTRACT

Disclosed herein is a method for imaging anisotropic media comprising selecting multiple points within the anisotropic media, which is to be imaged; determining an acoustic path between each selected point in the anisotropic media and a receiver position on the surface of the anisotropic media; calculating an acoustic wave velocity at all necessary points; determining an acoustic path length based on each selected point in the anisotropic media and the receiver position; determining a time delay for each acoustic wave between each image point and the receiver position on the surface of the anisotropic media; calculating a sum for each point selected based on the appropriate acoustic wave velocities and the acoustic path lengths; and generating an image of the anisotropic media using the coherent sums generated for each said image point selected.

20 Claims, 6 Drawing Sheets

OTHER PUBLICATIONS

Dubois et al. "Experimental Verification of the Effects of Optical Wavelength on the Amplitude of Laser Generated Ultrasound in Polymer-Matrix Composites" Ultrasonics 40 (2002) 809-812 Elsevier Science B.V.

Dubois et al. "Experimental Comparison Between Optical Spectroscopy and Laser-Ultrasound Generation in Polymer-Matrix Composites" Applied Physics Letters, vol. 79, No. 12, Sep. 17, 2001 pp. 1813-1815.

Greenstein et al. "A 2.5 MHz 2D Array with Z-Axis Electrically Conductive Backing" Hewlett-Packard Laboratories, Palo Alto, CA pp. 1-6.

* cited by examiner dt=130 nsec

METAL MATRIX COMPOSITE

METHOD FOR DETECTION OF DEFECTS IN ANISOTROPIC MATERIALS

BACKGROUND

In recent years, there has been a dramatic increase in the use of anisotropic media in structural applications such as in the aerospace industry. This anisotropy may be due to the use of reinforcing fibers in composites, directionally solidified materials or through the use of large scale single crystals in a composite matrix. Many tools that have been hitherto used for material property characterization are not sufficiently sensitive to locate defects present in directionally dependent materials. For example, conventional ultrasonic techniques have been used to locate defects in isotropic media but require a mechanical raster scan and are expensive, time consuming, and somewhat difficult to implement, particularly in manufactured articles having a complex curvature such as airfoils. To improve sensitivity in locating defects in attenuative media and articles with complex curvatures, focusing techniques are commonly used. Physical transducers are generally employed to facilitate focusing. These physical transducers employ a lens designed to coherently add acoustic signals from a localized target region in the manufactured article and simple shapes where simple lenses suffice. This approach is inadequate for use in anisotropic media.

Laser ultrasound involves the generation or detection of defects in manufactured articles by using lasers. The technique offers the potential of rapid, non-contact inspection. Typically, a laser source produces sound at a localized spot on the surface while a probe laser beam detects surface displacements or velocity. The detection is accomplished essentially at a point, resulting in unfocused detection. This method of detection is therefore not suitable for detecting defects in articles having complicated structures without suitable signal processing.

It is therefore desirable to determine methods wherein defects present in anisotropic structures having complicated articles and surfaces can be easily evaluated. It is further desirable to determine methods that can be advantageously used to characterize potential defects in anisotropic media during a real time examination in a manufacturing process.

SUMMARY

Disclosed herein is a method for imaging anisotropic media comprising selecting multiple points within the anisotropic media, which is to be imaged; determining an acoustic path between each selected point in the anisotropic media and a receiver position on the surface of the anisotropic media; calculating an acoustic wave velocity at all necessary points; determining an acoustic path length based on each selected point in the anisotropic media and the receiver position; determining a time delay for each acoustic wave between each image point and the receiver position on the surface of the anisotropic media; calculating a sum for each point selected based on the appropriate acoustic wave velocities and the acoustic path lengths; and generating an image of the anisotropic media using the coherent sums generated for each said image point selected.

Disclosed herein too is a method for imaging anisotropic media comprising slicing the anisotropic media; irradiating the anisotropic media with a point acoustic source; scanning the anisotropic media with a receiver to map out a sound field; determining a time delay in an acoustic wave from the sound field; and incorporating the time delay into an algorithm to provide enhanced resolution and sensitivity for the image.

DETAILED DESCRIPTION OF PREFERRED EMBODIMENTS

Figure 1:
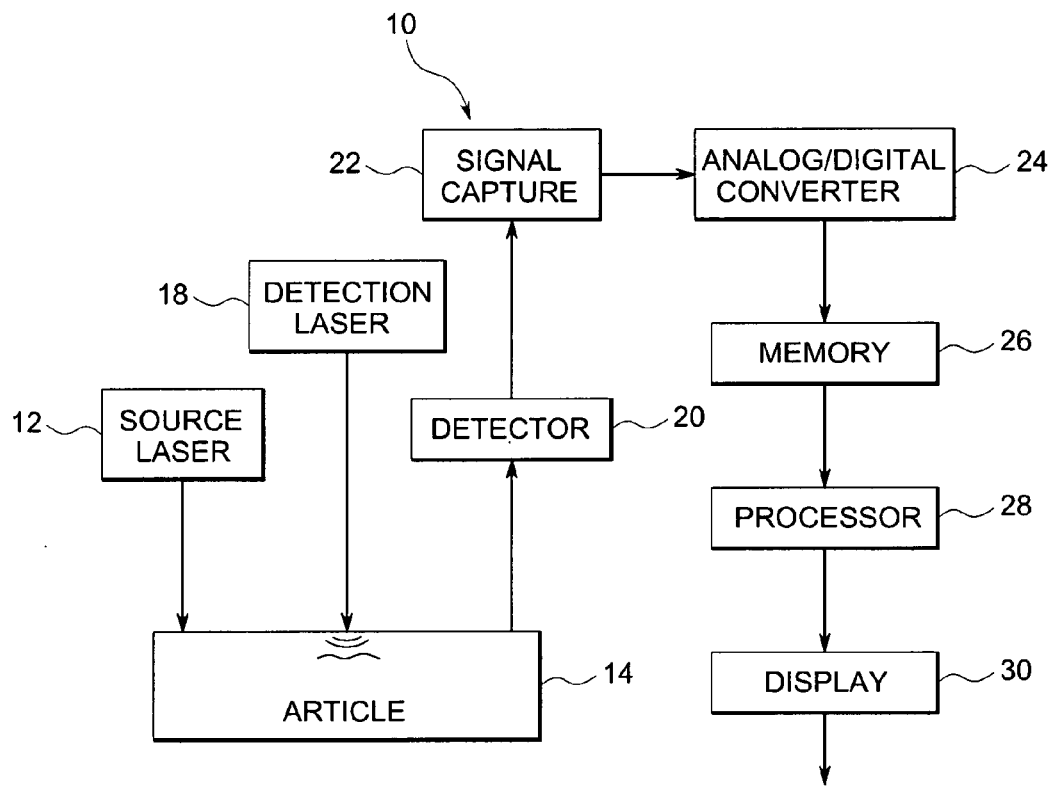
FIG. 1 shows one embodiment of a laser ultrasound inspection system.

Disclosed herein are methods to facilitate defect identification and determination in manufactured articles having an anisotropic structure. In one embodiment, the method is non-destructive and involves the use of calculations to identify how the sound wave will propagate in the article. This method, which is generally termed the empirical method, involves a reconstruction of the acoustic wave propagation delay through the article.

The method generally involves selecting multiple points within the anisotropic media which is to be imaged; determining an acoustic path between each selected point in the anisotropic media and a receiver position on the surface of the anisotropic media; calculating an acoustic wave velocity and an acoustic path length based on each selected point in the anisotropic media and the receiver position; determining a time delay for each acoustic wave between each image point and the receiver position on the surface of the anisotropic media; measuring a coherent sum for each point selected based on the acoustic wave velocity and the acoustic path length; and generating an image of the anisotropic media using the coherent sums generated for each said image point selected.

Acoustic wave velocity in anisotropic media is governed by the Christoffel equation. Beam skew, which is commonly observed in anisotropic media, must also be accounted for because the energy associated with the acoustic wave will not propagate in the direction of the acoustic wave normal. Once the velocities for each image point are determined, the acoustic path length for each image point is determined. Once the velocity and acoustic wave path length are determined for each image point, the time delay associated with that image point is readily calculated, and an improved image of the anisotropic material can be generated.

In another method, generally termed the experimental method, the delay may be estimated in a separate experiment wherein the article is sectioned or sliced. The sliced article is then subjected to a process such as laser ultrasound, or the like, to determine the acoustic wave propagation delay. The experimental method generally involves slicing up the article and measuring sound delays for various slices of the anisotropic article. This improved approach may be implemented with either conventional focused piezoelectric probes as synthetic aperture focusing technique transducers, with phased arrays, or with laser ultrasonics. This provides improved focusing and sensitivity in anisotropic materials.

Both of these methods are advantageous in that they have the resolution and sensitivity to resolve smaller defects in composites when compared with other commercially available methods. Improved defect detection and resolution is realized by incorporating accurate estimates for the time delays associated with acoustic wave transmission. Composite structures have become increasingly popular in recent years in applications such as such as aircraft wings and tail fins, fan blades, propellers, turbine nozzles, automobile exterior body panels and bumpers, or the like. In the case of aircraft, composites constitute a substantial fraction of the overall construction of the aircraft. Suitable composites are polymer-matrix composites having fibers such as graphite, carbon, glass fibers, or the like, incorporated into polymers such as epoxies, polyacetals, polyacrylics, polycarbonates polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, or the like. Other suitable composites are semi-crystalline alloys, single crystalline alloys such as titanium or nickel based alloys, and the like. In order to successfully manufacture such composites, a method of non-destructive testing is generally desired. Ultrasonic imaging provides an important method for identifying and quantifying such defects without destruction of the manufactured article. Common defects that may be detected by the present method of ultrasonic imaging are cracks, disbonds, corrosion, air bubbles, voids, pin-holes, air pockets, and the like.

The empirical method comprises selecting multiple points within the anisotropic article to be imaged, and determining the velocity of the acoustic wave between each image point selected and the receiver which is assumed to be on the surface of the article. The acoustic wave path length between each image point selected and the receiver is also determined. Next, using the acoustic wave velocity path length, the time delay for the acoustic wave between each image point selected and the receiver is determined. This may be accomplished by using knowledge of material constants as well as assembly plans for the article including ply maps and other engineering drawings. As a result, a coherent sum for all the acoustic wave generated by the acoustic wave source after the acoustic wave has passed through the anisotropic media can be generated and used to create an image of the anisotropic media.

In one embodiment, the empirical technique for measuring acoustic propagation delays generally utilizes arbitrary delays in acoustic wave transmission to create a synthetic transducer. This procedure is generally termed synthetic aperture focusing technique (SAFT). The synthetic transducer is created by multiple small elements that produce the arbitrary delays in acoustic wave transmission (acoustic propagation delays), which move the focal point about.

In the SAFT method as applied to isotropic media, an image is formed by summing the detected waveforms across the reception aperture j. This is shown in the equation (1) below $$I(x_i, y_i, z_i) = \sum_j U(x_i, y_i, z_i, \Delta t_{ij}) \tag{1}$$

where $\Delta t_{ij}$ is the round trip time delay for sound propagation from the observation point $(x_i, y_i, z_i)$ to the image point $(x_j, y_j, z_j)$. In the case of an isotropic material, this is given by equation (2)

$$\Delta t_{ij} = [(x_i-x_j)^2+(y_i-y_j)^2+(z_i-z_j)^2]^{1/2}/V_{material} \tag{2}$$

where $V_{material}$ is the speed of the acoustic wave in the isotropic material. To accurately form the image I of the article, a time delay is calculated for each point that is being imaged. In other words, time delays are calculated for each focal position, so SAFT may focus at all depths. In contrast, a physical transducer focuses only at a single depth. An improved image I may be obtained by appropriate apodization of the synthetic aperture and variations of aperture size with image depth.

In the apodization of the synthetic aperture, the data points representing the synthetic aperture are weighted differently to improve image resolution. For example, data points that represent measurements remote from the focal point can be weighted less than data points that represent measurements very close to the focal point. This technique improves accuracy by suppressing background noise and eliminating artifacts that arise near the edge of the aperture. Windowing functions such as, for example, the Blackmann, Bartlett, Connes, Cosine, Gaussian, Hamming, Hanning, uniform, and Welch windows may be used to weight the various data points making up the synthetic aperture.

Unlike isotropic media where group and phase velocities of an acoustic wave coincide with one another, energy propagation in an anisotropic media will not coincide with the wave normal unless the propagation direction is along a symmetry axis. This phenomenon is known as energy flux deviation or beam skew. Acoustic energy does not necessarily propagate in the direction normal to the face of the transducer (wave normal direction) as happens with isotropic media, but will rather be skewed at an oblique angle relative to the wave normal. In particular, any SAFT reconstruction algorithm due to anisotropy must account for both beam skew effects as well as the intrinsic variations in acoustic velocity with the direction of propagation. Wave propagation in anisotropic media is governed by the Christoffel equation, which yields the three possible phase velocities (one for each mode of propagation) for any chosen wave normal. The Christoffel equation, which governs acoustic wave propagation in anisotropic media is given by equation (3)

$$(C_{ijkl}l_jl_l - \rho v^2 \delta_{ik}) \alpha_k = 0 \tag{3}$$

where $C_{ijkl}$=components of the stiffness tensor; $l_j$=components of wave normal; $l_l$=components of particle displacement; $\rho$=density; $v$=phase velocity; $\delta_{ik}$=components of identity tensor. The image is obtained by calculating the sound velocity as a function of direction in every location of the article using the Christoffel equation.

For any given propagation direction 1, this yields an eigenvalue problem with three possible phase velocities ($V_{material}$), each associated with a polarization vector α. Unlike isotropic media where pure modes propagate and wherein α and 1 are either parallel (longitudinal) or perpendicular (transverse) to one another, in anisotropic media α and 1 are generally neither parallel or perpendicular to one another. The bulk waves which propagate will not be pure modes but rather will have some of the character of both longitudinal and transverse vibration. They are referred to as being quasi-longitudinal and quasi-transverse waves. The beam skew as detailed above adds a further degree of complexity to this situation. Energy propagation is therefore governed by the following equation (4)

$$Sj = \frac{C_{ijkl}\alpha_i\alpha_k l_l}{\rho\upsilon} \quad (4)$$

where S is the energy propagation vector and S.l=υ. The beam skew phenomenon therefore has important consequences in the design of a reliable SAFT imaging algorithm.

While the effects of anisotropy generally complicate the analysis and thus the calculations, the problem can be converted into a tractable one provided the baseline material acoustic properties are known. The baseline material acoustic properties may be obtained from a knowledge of the fundamental properties of the materials of the article. Additional acoustic properties may be determined from the engineering drawings used to manufacture the parts. The key element in the design of a reliable SAFT algorithm is the ability to accurately model the acoustic transit times between any reflector (e.g., microstructural defects) within the manufactured article and any potential receiver (detector) position on the surface of the article. For isotropic, homogeneous media, the calculation is straightforward since the acoustic rays will travel along a straight-line ray path and delays can be calculated from equation (2). For inhomogeneous, anisotropic media, the ray paths will still be along straight lines, but the beam skew phenomenon has to be accounted for. The actual calculation of acoustic transit times between a postulated source and receiver is complicated by the observation that the wave normal for the acoustic ray path between the source and receiver can not be simply determined by the spatial locations of the two end points of the ray path.

In order to estimate the actual acoustic transit times between any point within the article and the detector, an iterative scheme to identify the correct wave normal is generally preferred. A possible direct path for the wave is first postulated and the wave normal to this postulated path may be adjusted using a least squares minimization routine to adjust the postulated wave normal and consequently the ray to the point where the ray trajectory intersects the sensing surface at a point where the receiver location is desired. An improved estimate of the measured time delays for the acoustic waves can be obtained from knowledge of fundamental material properties, assembly plans such as ply maps, and engineering drawings used to design and manufacture the articles. Using this methodology it is possible to design a SAFT correction scheme for anisotropic media in a manner analogous with the SAFT technique for isotropic media.

Once this is established, the group velocities and beam skew angles can be readily calculated. For many materials of interest, notably curved composite articles, the local inhomogeneity in material properties introduced by microstructural variations such as ply curvature produces an additional complicating factor in imaging. Acoustic rays, in inhomogeneous media will not travel along straight-line paths, but will bend. This increases the acoustic path length and hence transit time. In order to rectify this, acoustic ray tracers may be utilized. The acoustic ray tracers are based on a localized form of Snell's law or a variational calculus formulation based on Fermat's principle. The sum thus obtained may be coherent, incoherent or partially coherent. Alternatively, one can construct a full field finite difference model and track the wavefronts associated with each mode of propagation directly. While all these approaches accurately model acoustic ray paths in inhomogeneous anisotropic media, Snell's law based ray tracers are somewhat easier to implement and are the preferred method of implementation.

Thus the use of an iterative scheme coupled with use of acoustic tracers may be used to obtain accurate wave paths and acoustic transit times, which in turn may be used to obtain an accurate sound propagation model of the article.

In the experimental method, which is a destructive technique for evaluating the time delays, the article is sliced up and subjected to inspection in a laser ultrasound inspection system to measure delays and determine acoustic wave paths. The determination of the acoustic wave paths, may then be advantageously used to be used to obtain an accurate sound propagation model of the article. This is accomplished by using the aforementioned equation (2). The equation may be modified by methods such as apodization of the reconstruction aperture, asymmetric apertures, or apertures with non-coincident sources and receivers, multiple sources and/or receivers, and dynamic zooming of the aperture with depth. A standard time delay SAFT code may also optionally be used where a look up table is experimentally measured and this can be used to reflect the article anisotropy.

In one exemplary embodiment, FIG. 1 shows a block diagram of a laser ultrasound inspection system 10. In the laser ultrasound inspection system 10, the surface of an article is illuminated (scanned) with either a single source laser or a multiple source laser 12. A preferred ultrasound inspection system 10 comprises a phased array ultrasound system having multiple transmitters and multiple receivers (detectors) 20. The article may be an engineering material such as, for example, a metal aircraft skin or a graphite-epoxy turbine blade. The source laser 12 irradiates the article 14 with a laser beam along its surface at a plurality of scanning positions. The laser beam generated from the source laser 12 typically has a relatively high energy, for example on the order of $5\times10^8$ W/cm² or less.

Examples of lasers include dye lasers, tunable lasers, pulsed lasers, gas lasers, excimer lasers, fiber lasers, diode lasers, free-electron lasers, and solid-state lasers. Examples of dye lasers include continuous wave, excimer-pumped, flashlamp-pumped, nitrogen-pumped, pulsed, doubled-Nd:YAG-pumped, and copper-vapor-pumped. Examples of gas lasers include ion, metal vapor, excimer, far-infrared, mixed gas, carbon monoxide, argon fluoride, argon ion, carbon dioxide, deuterium fluoride, fluoride/fluorine, helium-gold, helium-neon, helium-silver, hydrogen-fluoride, krypton, krypton chloride, krypton fluoride, neon-copper, nitrogen, nitrogen oxide, xenon, xenon chloride, and xenon helium. Examples of excimer lasers include argon fluoride, fluorine, krypton fluoride, xenon bromide, xenon chloride and xenon fluoride. Examples of fiber lasers include continuous wave and laser-pumped. Examples of diode lasers include continuous wave, current-tuned, linear array-quasi continuous wave, temperature stabilized, tunable, visible, AlGaInP/

GaAs, GaAlAs/GaAs, GaAlAs, GaAs, InGaAs, InGaAs/InP, and lead salt. Examples of solid-state lasers include color center, flashlamp-pumped, continuous wave, diode-laser-pumped, CW-pumped, pulsed, Cr:LiCAF, Cr:LiSAF, CTh: YAG, Er:YAG, Er:YLF, forsterite, Ho:YAG, $KnBO_3$, KBO, LiF, Nd:glass, Nd:LSB, Nd:YAB, Nd:YAG, Nd:YAG/KTP, Nd:YALO, Nd:YLF, ruby, Th:YAG/Ti:YAG, Ti:sapphire, Tm:LuAG, Tm:YAG, Tm:YLF, and $YVO_4$.

Ultrasonic waves are generated by the laser beam by non-destructive local heating of the article to create expansion and a strain wave which then propagates through the article 14. The generated ultrasonic waves propagate through the article 14 and are reflected back to the scanning position by a reflector 16 such as a defect located within the article or along the surface of the article. As the reflected ultrasonic waves return to the scanning position, a detection laser 18 is used to detect either displacement or velocity at the surface by simultaneously irradiating the surface of the article with another laser beam. The laser beam generated from the detection laser 18 has line width, stability, and fluence suitable for interferometric detection. A detector 20, typically a sensitive interferometric detector, detects and amplifies the displacement or velocity signals and outputs the signals to a signal capture 22.

As stated above, it is desirable for the system 10 to have a phased array transducer, having multiple transmitters 10 and detectors 20. In one embodiment, the transducer array is configured as a sparse array, in which certain elements of the array are used for transmitting laser ultrasound, and other elements of the array are used to receive ultrasound. In another embodiment, the transmit and receive elements in a sparse array have different structure (e.g., geometry), each optimized for their respective transmitting and receiving functions. In a further embodiment, a transducer is configured solely for transmitting ultrasound, for use with a second transducer configured solely to receive ultrasound. The transmit and receive transducers can have the same or different array geometry. In this embodiment, the article under investigation is placed between the transmit and receive transducers.

The ultrasonic receiver receives and processes input signals. In one embodiment, the receiver has a frequency response of 0.5 to 30 MHz at −6 dB and 40 dB gain. The receiver provides 0 to 98 dB of gain in increments of 0.5 dB (−40 dB to +58 dB).

In another optional embodiment, a matched filter can be constructed which is dependent on propagation distance and direction for an anisotropic material. In an anisotropic material, the velocity of sound is dependent upon the direction of propagation. The matched filter for an anisotropic material is constructed by measuring a response such as a surface displacement or velocity as a function of distance from the source and as a function of propagation direction. The matched filter which is a 3-dimensional matched filter, is applied in a manner effective to remove dispersions in anisotropic materials which are dependent not only on distance but also on propagation direction. Rather than utilizing a single compensated waveform to image in all directions at a particular distance, each direction has a unique filter data point associated with it.

In yet another embodiment, the matched filter can be modified to filter all but a particular mode of propagation. In thin structures, it is common for one mode of propagation (e.g., the antisymmetric mode) to be more sensitive to a particular type of defect than other modes of propagation. Sensitivity can be quantified, for example, in terms of the amplitude of the reflected signal for a particular mode. A more sensitive mode of propagation for a particular type of defect has a greater reflected signal amplitude. The receiver may optionally contain high pass and low pass filters. The filters may be used separately or in combination to produce a specific band pass filter. The receiver includes sufficient sensitivity and noise level capabilities. It is generally desirable for the noise level to not exceed 40% grass level on screen at maximum gain. Each receiver channel may also include a digital amplitude correction (DAC) if desired. The DAC is active over the entire acquisition time, with each channel being independently controllable.

The amplified signals, which represent laser ultrasound waveform data, are digitized by a converter 24 and stored in a memory 26. The laser ultrasound waveform data stored in the memory 26 form a scan data set comprising a plurality of data points which represent a motion of the article, such as surface displacement or velocity, as a function of time or frequency, at a plurality of detection points. The scan data set stored in the memory is processed by a processor 28. The processor reconstructs an image of the article that may be displayed on a display 30. While the aforementioned embodiments pertaining to the system 10 generally describe an ultrasound system having phased array transducers, it is also possible to use the approach with conventional focused piezoelectric probes as SAFT transducers.

The sensitivity of laser ultrasound imaging can be significantly improved with the synthetic aperture focusing technique. The laser detector 20 itself is typically sensitive only to the normal component of motion and does not differentiate between different directions of arrival of the reflected ultrasonic waves. The laser detector 20 is thus unable to focus and therefore identify the exact spatial location of any reflectors 16 within the article 14, which give rise to the detected signals. In synthetic aperture focusing, however, reflected signals obtained at different scan positions are coherently summed by delaying each signal a specified time period to focus the reflected signal, which diverges from the reflector 16. Synthetic aperture focusing allows the signals reflected in different directions from the reflector to be synthetically focused to produce an image with improved resolution.

Figure 2A:
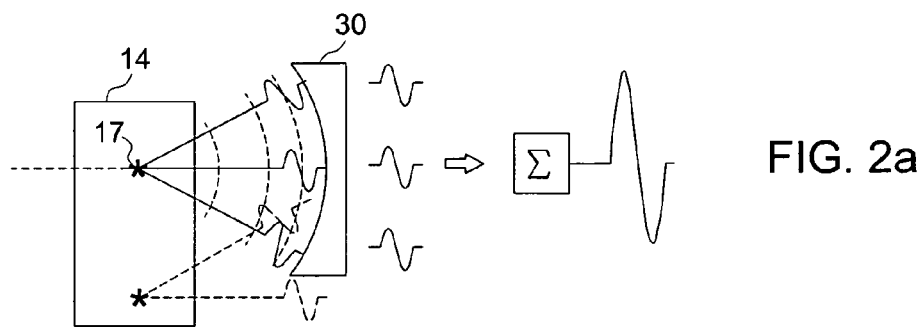
FIG. 2a, is a schematic depicting a physically focused transducer summing wavefronts arriving across the face of the transducer.
Figure 2B:
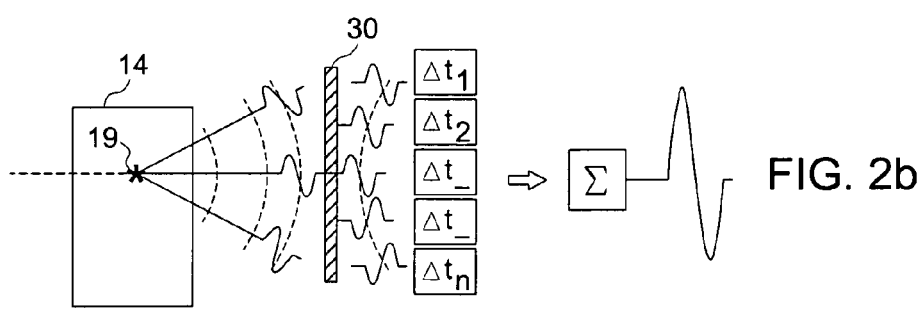
FIG. 2b is a schematic illustrating the synthetic aperture focusing technique (SAFT)

FIGS. 2a and 2b illustrate methods of focusing waves reflected from a reflector 16. As shown in FIG. 2a, a physically focused transducer 30 sums wavefronts arriving across the face of the transducer. A coherent sum is produced for signals arriving in phase from a localized region 17 (the focus), and an incoherent sum is produced for other signals. The physical focus can be realized either with a shaped lens or with a shaped transducer element. FIG. 2b illustrates the synthetic aperture focusing technique (SAFT). In FIG. 2b, a generalized or synthetic transducer is formed by creating arbitrary delays to move the focal point 19 about. The synthetic aperture focusing technique may utilize a single transmitter with a diverging beam and a single receiver, which are scanned across the surface of the article to cover the desired aperture. The transducer location and the speed of sound through the article are used to create a focused image.

Figure 3:
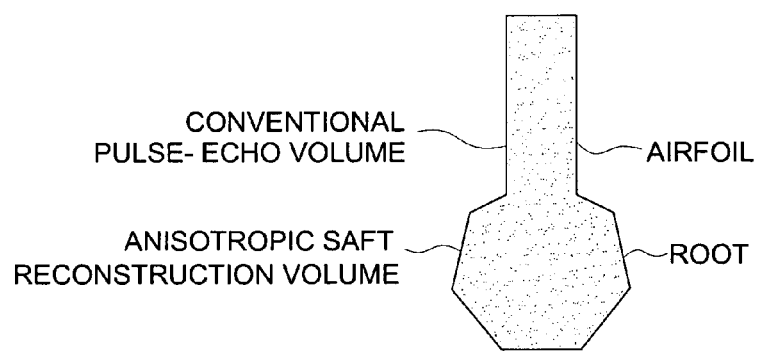
FIG. 3 is a schematic of the composite engine fan blade.

In one embodiment, in one manner of proceeding with the experimental method, a thick composite article comprising a composite engine fan blade (wide chord fan blade) may be examined and imaged using the technique detailed above. A schematic of the composite engine fan blade is shown in FIG. 3. While laser ultrasound pulse-echo imaging may be utilized in the airfoil regions and outside the root where penetration is adequate, in the deeper regions, anisotropic SAFT may be advantageously used to compensate for beam steering and distortion. By confining SAFT to the deeper regions, the amount of computation is minimized. If desired, the same apparatus may be used to image the entire structure shown in the FIG. 3 by using a larger spot-size and scan step-size in the airfoil region and a smaller spot and step-size to produce adequate beam spread in the illuminating beam and resolution in the reconstructed image.

Figure 4:
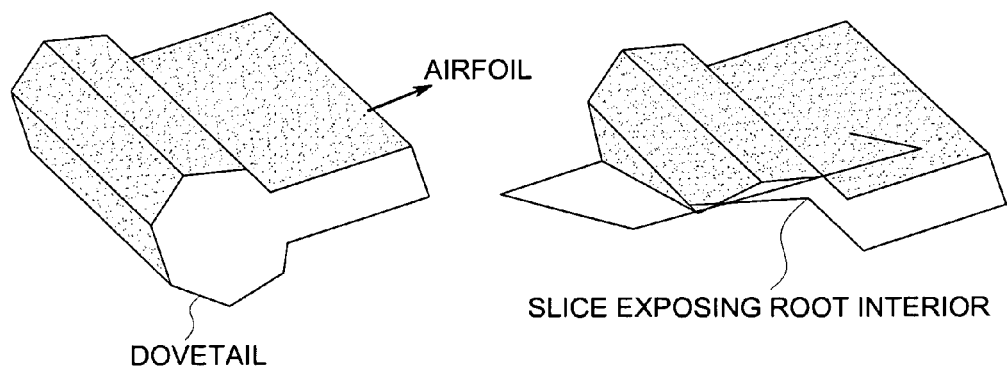
FIG. 4 depicts how the composite engine fan blade is sliced exposing a section of the interior.
Figure 5:
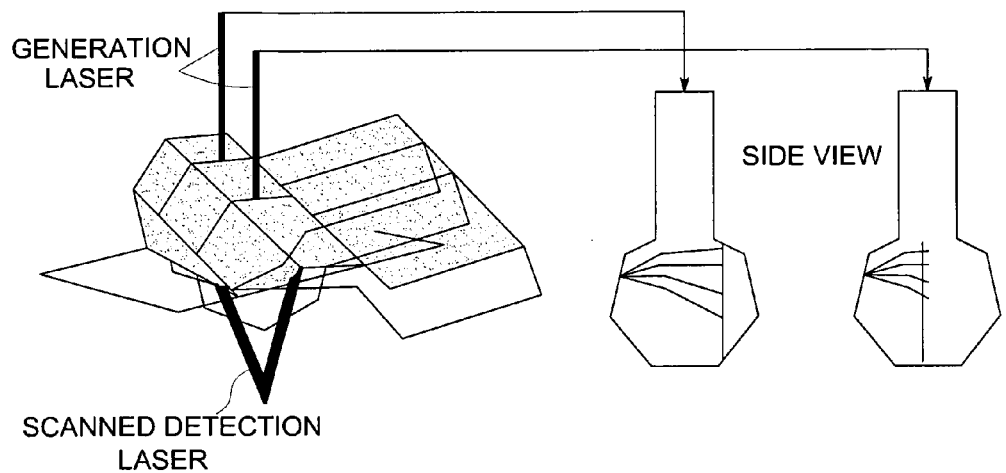
FIG. 5 shows the measurement of the sound field in the direction along the long axis of the blade.
Figure 6:
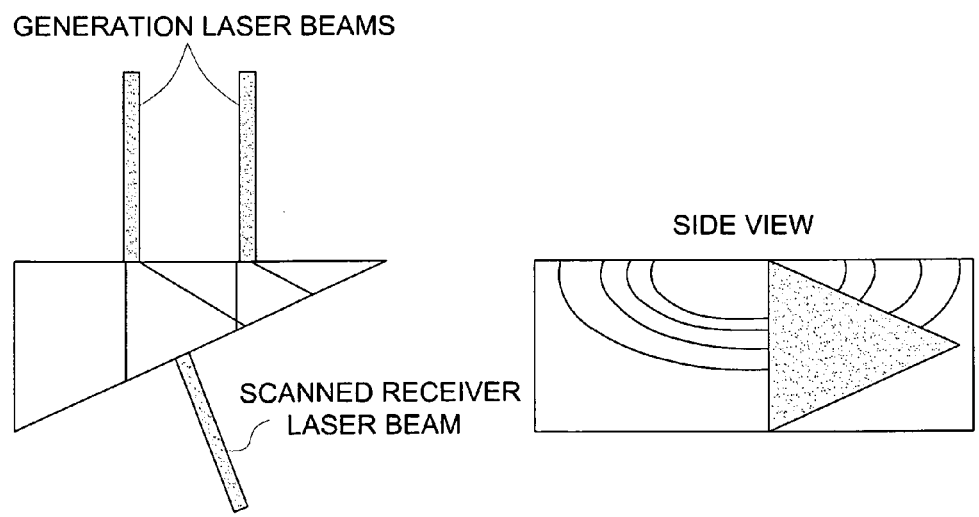
FIG. 6 shows the acoustic mapping in the orthogonal direction and the filling out of the sound delay look-up table.

FIG. 4 shows how this can be done for the wide chord fan blade. As seen in the FIG. 4, a transverse slice is made exposing a section of the interior. This slice spans the range of depths that encompasses the proposed region to be imaged by SAFT. The sound field is then mapped as shown in FIGS. 5 and 6. At each source laser position, the receiver laser beam is scanned on the opposite face of the to map out the sound field for the engine fan blade. FIG. 5 shows the measurement of the sound field in the direction along the long axis of the blade. FIG. 6 shows the mapping in the orthogonal direction and the filling out of the sound delay look-up table. The laser ultrasound is generally only filled out to the size of the aperture to be used later. Measurement of the sound field can be used to estimate the size of the maximum useable aperture and to calculate the optimum size for the source laser spot to fill those angles with sound. Although the mapping is accomplished here with laser ultrasound, conventional or phased array transducers could also have been used.

Figure 7:
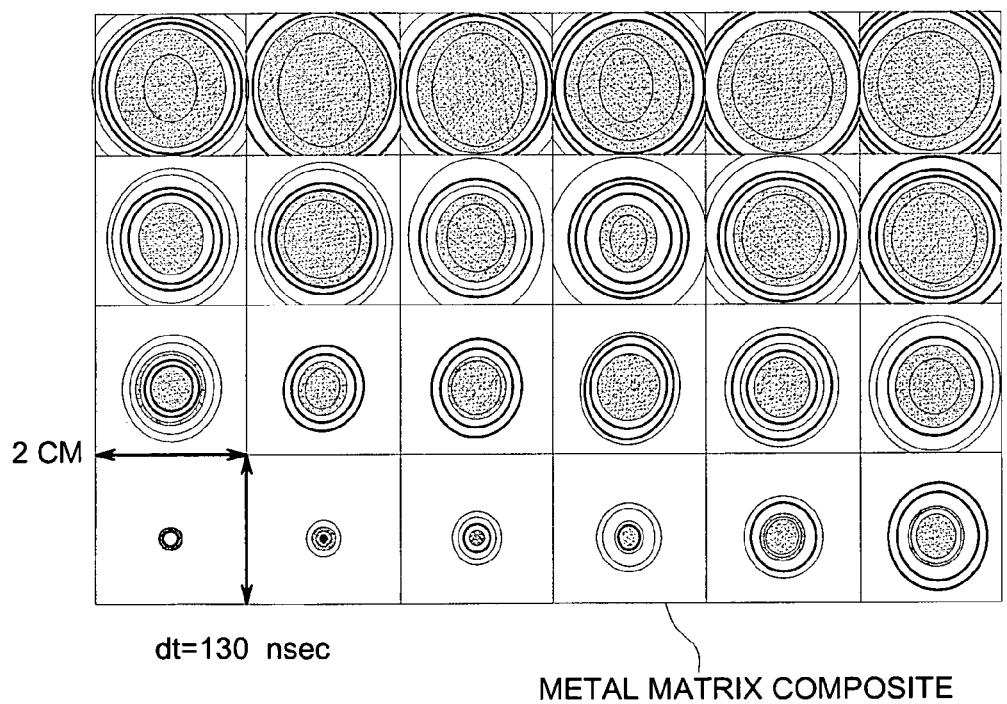
FIG. 7 is an image of a sound field shown at various time intervals, wherein delays in acoustic wave propagation may be read from the data.

FIG. 7 shows the results of a simple experimental demonstration of this mapping technique performed on a piece of metal matrix composite. A laser ultrasound source was repeatedly fired on one side of the part while a receiver was scanned on the opposite face. The acquired data can be replayed as a movie, showing sound field movement through the part. This approach was developed to measure anisotropy and to measure empirical sound delays for exactly this sort of application—SAFT imaging in anisotropic materials. Although the delays were measured, reconstructions were not performed in the first phase of the program. The data for a graphite/epoxy part would be obtained in the same manner.

In general, as detailed above, sound propagation delays are key to forming a focused image and are measured using a scanned laser ultrasound receiver and a fabricated focal standard. This same standard can be achieved in using a conventional inspection where the conventional piezoelectric transducer would be repeatedly fired and the deep part sound field measured. A standard time delay SAFT code would be used where the look up table would be experimentally measured and reflect the true part anisotropy rather than derived from a model assuming isotropic sound velocity as is now done.

The following example, which is meant to be exemplary, not limiting, illustrates compositions and methods of imaging some of the anisotropic composites described herein.

EXAMPLE

This example was undertaken to demonstrate a SAFT correction function for an isotropic material versus a quasi-isotropic laminate, a uni-directionally reinforced composite, or a single crystal engine alloy. This example demonstrates how a model calculation may be used to determine acoustic wave propagation delays. This method uses the empirical method detailed above to calculate the acoustic wave propagation delays. The isotropic material was aluminum. The quasi-isotropic laminate had multiple ply directions and was manufactured from a graphite-epoxy composite. The uni-directionally reinforced composite utilized plies aligned in a single direction and was also manufactured from a graphite-epoxy composite. The single crystal engine alloy comprised a nickel super-alloy.

Figure 8:
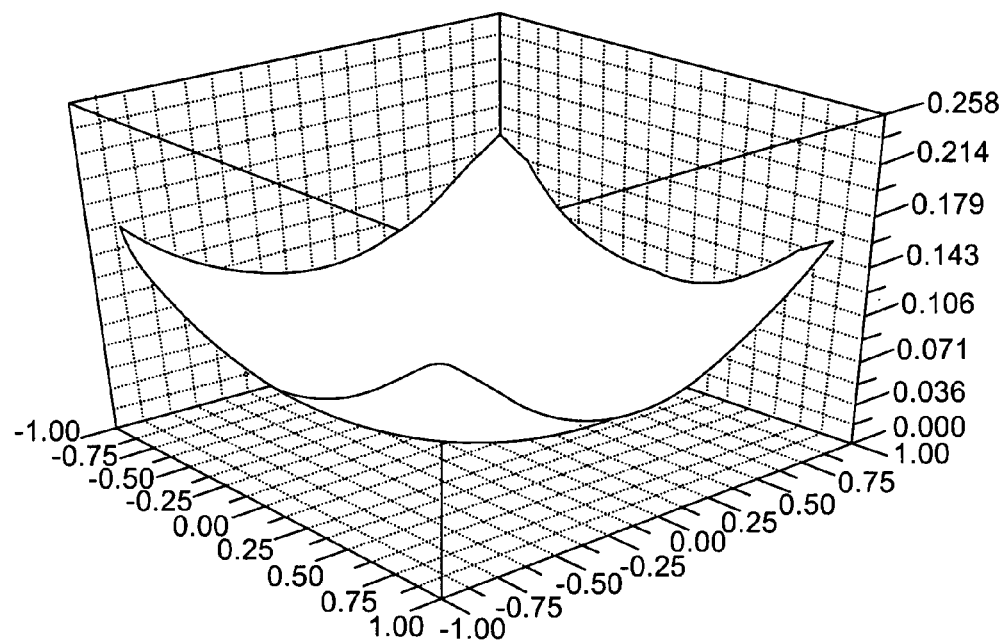
FIG. 8 shows the SAFT time shift as a function of surface position for the aluminum.
Figure 9:
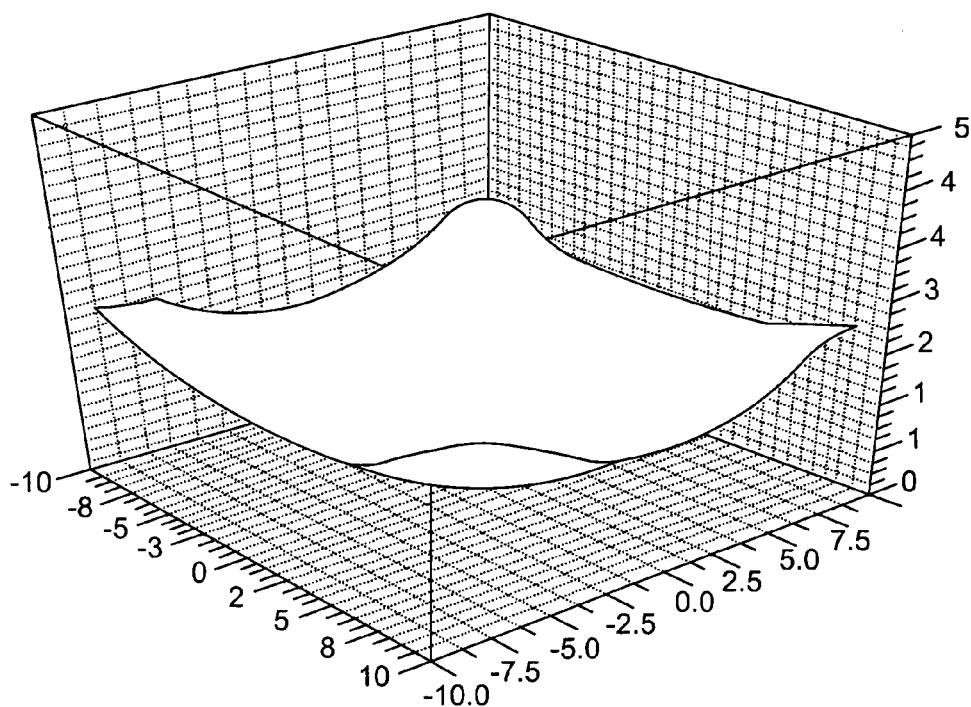
FIG. 9, shows the SAFT time shift as a function of surface position for the quasi-isotropic ($\pi/4$) laminate.
Figure 10:
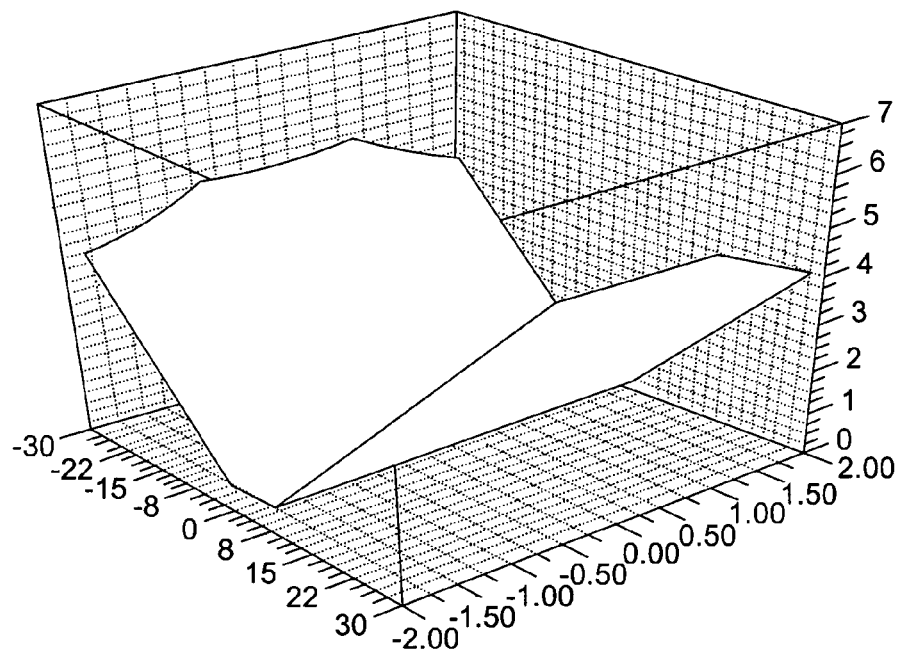
FIG. 10 shows the SAFT time shift as a function of surface position for the unidirectionally reinforced composite.
Figure 11:
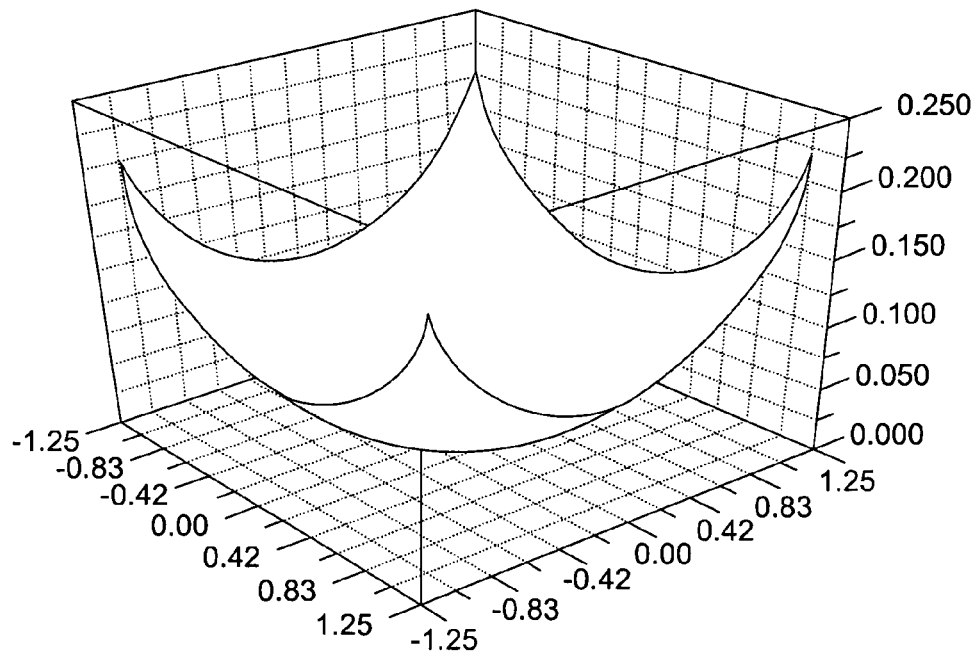
FIG. 11 shows the SAFT time shift as a function of surface position for the cubic single crystal alloy.

The difference in acoustic wave time shift for the aforementioned materials is evident by comparing FIGS. 7, 8, 9 and 10. FIG. 7 shows the SAFT time shift as a function of surface position for the aluminum, while FIGS. 8, 9 and 10 show similar calculations for the quasi-isotropic ($\pi/4$) laminate, the unidirectionally reinforced composite and the cubic single crystal alloy. Clearly, the effect of the material's anisotropy is most pronounced for the unidirectionally reinforced composite of FIG. 9.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for imaging anisotropic media comprising:
   selecting multiple points within the anisotropic media, which is to be imaged, and determining an acoustic path between each selected point in the anisotropic media and a receiver position on the surface of the anisotropic media;
   calculating an acoustic wave velocity at the selected points, and determining an acoustic path length based on each selected point in the anisotropic media and the receiver position;
   determining a time delay for each acoustic wave between each selected point and the receiver position on the surface of the anisotropic media;
   calculating a sum for each selected point based on the acoustic wave velocities, the acoustic path lengths, and the time delays; and
   generating an image of the anisotropic media using the sums generated for each selected point.

2. The method of claim 1, wherein the determining the acoustic path between each selected point in the anisotropic media and a receiver position on the surface of the anisotropic media comprises postulating a direct path for the wave.

3. The method of claim 1, wherein the determining the acoustic path between each selected point in the anisotropic media and a receiver position further comprises adjusting the wave normal to the postulated path using a least squares minimization routine such that the wave normal is adjusted to a point where the ray trajectory intersects the sensing surface at a point where the receiver location is desired.

4. The method of claim 1, wherein the calculating the acoustic wave velocity in any direction is accomplished by solving a Christoffel equation.

5. The method of claim 1, wherein the calculating the acoustic wave velocity further comprises determining phase and group velocities, and further wherein the phase and group velocities are determined by a knowledge of fundamental material properties of the anisotropic media.

6. The method of claim 5, wherein the phase and group velocities in the anisotropic media are determined from engineering drawings used to design and manufacture parts.

7. The method of claim 1, wherein the calculating the acoustic wave velocity is accomplished by further determining the beam skew.

8. The method of claim 1, wherein the beam skew may be determined by a localized form of Snell's law, a variational calculus formulation based on Fermat's principle, or a full field finite difference model that tracks the wavefronts associated with each mode of propagation.

9. The method of claim 1, wherein the calculating a sum involves calculating a coherent sum.

10. The method of claim 1, wherein the calculating a sum involves calculating an incoherent sum.

11. The method of claim 1, wherein the calculating a sum involves calculating a partially coherent sum.

12. A method for imaging anisotropic media comprising:
slicing the anisotropic media;
irradiating the anisotropic media with a point acoustic source;
scanning the anisotropic media with a receiver to map out a sound field;
determining time delays in an acoustic wave from the sound field, the time delays being based upon the acoustic paths between points in isotropic materials within the anisotropic media and a receiver position; and
incorporating the time delays into an algorithm to provide enhanced resolution and sensitivity for an image of the anisotropic media.

13. The method of claim 12, wherein the algorithm is represented by the equations (1):

$$I(x_i, y_i, z_i) = \sum_j U(x_i, y_i, z_i, \Delta t_{ij}) \quad (1)$$

where $\Delta_{ij}$ is the round trip time delay for sound propagation from the observation point $(x_i, y_i, z_i)$ to the image point $(x_j, y_j, z_j)$, and by equation (2)

$$\Delta t_{ij} = \frac{1}{2}[(x_i - x_j)^2 + (y_i - y_j)^2 + (z_i - z_j)^2]^{1/2} / V_{material} \quad (2)$$

where $V_{material}$ is the speed of the acoustic wave in the isotropic materials within the anisotropic media.

14. The method of claim 12, wherein the acoustic point source is a laser, a conventional array transducer, or a phased array transducer.

15. A method for imaging anisotropic media comprising:
selecting multiple points in isotropic materials within the anisotropic media, and determining an acoustic path between each selected point in the anisotropic media and a receiver position on the surface of the anisotropic media;
irradiating the anisotropic media with a point acoustic source;
scanning the anisotropic media with a receiver to map out a sound field;
determining time delays in an acoustic wave from the sound field, the time delays being based upon the acoustic paths between the selected points and a receiver position; and
incorporating the time delays into an algorithm to provide enhanced resolution and sensitivity for an image of the anisotropic media.

16. The method of claim 15, wherein the determining the acoustic path between each selected point in the anisotropic media and a receiver position on the surface of the anisotropic media comprises postulating a direct path for the wave.

17. The method of claim 15, wherein determining the acoustic path between each selected point in the anisotropic media and a receiver position further comprises adjusting the wave normal to the postulated path using a least squares minimization routine such that the wave normal is adjusted to a point where a ray trajectory intersects a sensing surface at a point where the receiver position is desired.

18. The method of claim 15, wherein the algorithm is represented by the equations (1):

$$I(x_i, y_i, z_i) = \sum_j U(x_i, y_i, z_i, \Delta t_{ij}) \quad (1)$$

where $\Delta t_{ij}$ is the round trip time delay for sound propagation from the observation point $(x_i, y_i, z_i)$ to the image point $(x_j, y_j, z_j)$, and by equation (2)

$$\Delta t_{ij} = \frac{1}{2}[(x_i - x_j)^2 + (y_i - y_j)^2 + (z_i - z_j)^2]^{1/2} / V_{material} \quad (2)$$

where $V_{material}$ is the speed of the acoustic wave in the isotropic materials within the anisotropic media.

19. The method of claim 15, wherein the acoustic point source is a laser, a conventional array transducer, or a phased array transducer.

20. The method of claim 15, wherein the determining the time delays comprises employing ply maps, or engineering drawings.

* * * * *